(12) United States Patent
Park

(10) Patent No.: US 12,714,601 B2
(45) Date of Patent: Aug. 25, 2026

(54) SURGICAL SCISSORS FOR INCISING ANTERIOR CAPSULE OF LENS

(71) Applicant: Hyungju Park, Seoul (KR)

(72) Inventor: Hyungju Park, Seoul (KR)

( * ) Notice: Subject to any disclaimer, the term of this patent is extended or adjusted under 35 U.S.C. 154(b) by 14 days.

(21) Appl. No.: 19/083,726

(22) Filed: Mar. 19, 2025

(65) Prior Publication Data

US 2025/0213392 A1 Jul. 3, 2025

Related U.S. Application Data

(63) Continuation of application No. PCT/KR2024/006559, filed on May 14, 2024.

(30) Foreign Application Priority Data

Jun. 9, 2023 (KR) ........................ 10-2023-0073952

(51) Int. Cl.
*A61F 9/007* (2006.01)
*A61B 17/3201* (2006.01)

(52) U.S. Cl.
CPC ...... *A61F 9/00754* (2013.01); *A61B 17/3201* (2013.01)

(58) Field of Classification Search
CPC ......... A61B 17/3201; A61B 2017/2918; A61F 9/00754; A61F 9/00736; A61F 9/007; A61F 2/1664; A61F 9/00763
See application file for complete search history.

(56) References Cited

U.S. PATENT DOCUMENTS

2005/0209624 A1* 9/2005 Vijay ................. A61B 17/3201 606/174

OTHER PUBLICATIONS

Translation of PCT Written Opinion in PCT/KR2024/006559 (Year: 2024).*

* cited by examiner

*Primary Examiner* — Katherine M Shi
(74) *Attorney, Agent, or Firm* — Dinsmore & Shohl LLP; Yongsok Choi, Esq.

(57) ABSTRACT

Surgical scissors for incising anterior capsule of lens include first and second levers extending in front-rear direction and rotation shaft rotatably connecting first and second levers to each other. First lever includes: first handle formed at rear portion with reference to rotation shaft; first blade having first non-cutting part formed at front portion with reference to rotation shaft and extending forward, and first cutting part protruding in one side direction crossing front-rear direction and up-down direction from front end of first non-cutting part. Second lever includes: second handle formed at rear portion with reference to rotation shaft and capable of being spaced downward from first handle; second blade having second non-cutting part formed at front portion with reference to rotation shaft and extending forward, and second cutting part protruding in one side direction from front end of second non-cutting part to be in contact with first cutting part.

9 Claims, 6 Drawing Sheets

121
140
110
122

141 140 110

122 121

122a

122b

SURGICAL SCISSORS FOR INCISING ANTERIOR CAPSULE OF LENS

CROSS-REFERENCE TO RELATED APPLICATION

This application is a bypass continuation application of International Patent Application No. PCT/KR2024/006559 having an international filing date of May 14, 2024 and designating the United States, the international application being based upon and claiming the benefit of priority from Korean Patent Application No. 10-2023-0073952 filed on Jun. 9, 2023, the entire contents of which are incorporated herein by reference.

TECHNICAL FIELD

The present disclosure relates to surgical scissors for incising an anterior capsule of a lens.

BACKGROUND

A transparent lens inside the human eye plays an important role in focusing on an object to provide clear vision. The transparent lens may become cloudy due to aging, eye inflammation, or trauma. Accordingly, a cataract, a type of ophthalmic disease, may develop. If a cataract progresses to the point of causing discomfort in daily life, surgery should be considered as medication does not improve symptoms.

Cataract surgery is performed in a manner of making a small hole in the black or white part of an eye, inserting an ultrasonic device into the hole to suction out a cataractous lens, and then inserting a permanent artificial lens in its place. Specifically, continuous curvilinear capsulorrhexis (CCC) is performed by making an incision in a cornea, injecting viscoelastics having a predetermined viscosity between the cornea and a lens, and making a circular incision in an anterior capsule located at the front of a lens capsule. In this process, the viscoelastics are injected between the cornea and the lens to form a predetermined space to facilitate an insertion of a surgical instrument, an artificial lens, or the like. Then, as the viscoelastics are injected through an incised opening of the anterior capsule, the cataractous lens is suctioned using ultrasound. In this process, the viscoelastics prevent the lens capsule from shrinking due to a lack of moisture caused by the incision of the anterior capsule of the lens, and serve to maintain the lens capsule in a certain shape. Thereafter, the artificial lens is inserted and attached to the lens capsule to be fixed. The viscoelastics may be suctioned and removed before and after the insertion of the artificial lens.

Since the lens capsule is made of fiber, the lens capsule has a property of contracting over time. If an opening formed in the anterior capsule of the lens is not located at the center thereof but is biased to a periphery portion, the shrinking force of the lens capsule becomes uneven and may thus cause the inserted artificial lens to bend. Therefore, since the anterior capsule of the lens needs to be incised so that the opening is located at the center, the opening is additionally incised into a shape close to a circular shape.

SUMMARY

However, conventionally, an incision part of incision scissors has a straight shape, and thus an entry direction in which the incision scissors enter (e.g., an approximate outer radial direction of an opening) is substantially perpendicular to an incision direction in which an incision is to be made (e.g., an approximate circumferential direction of a circular opening). Therefore, it is very difficult to additionally incise the edge of an opening into a shape close to a circular shape. In some cases, a straight cut may be formed outside the incision direction, or the incision may be made larger than an opening that needs to be incised. This may cause the position of an artificial lens to shift or the shape of the artificial lens to be deformed.

Embodiments of the present disclosure improve or solve at least some of the problems of conventional straight-type incision scissors. To this end, multiple embodiments provide surgical scissors for incising an anterior capsule of a lens, the surgical scissors including a first cutting part and a second cutting part arranged in a direction crossing an entry direction of incision scissors.

Embodiments according to one aspect of the preset disclosure are directed to surgical scissors for incising an anterior capsule of a lens. The surgical scissors for incising an anterior capsule of a lens according to an exemplary embodiment include: a first lever extending in a front-rear direction; a second lever extending in the front-rear direction; and a rotation shaft configured to rotatably connect the first lever and the second lever to each other. The first lever includes: a first handle formed at a rear portion with reference to the rotation shaft; and a first blade having a first non-cutting part formed at a front portion with reference to the rotation shaft and extending forward, and a first cutting part protruding in one side direction crossing the front-rear direction and an up-down direction from a front end of the first non-cutting part. The second lever includes: a second handle formed at the rear portion with reference to the rotation shaft and capable of being spaced downward from the first handle; and a second blade having a second non-cutting part formed at a front portion with reference to the rotation shaft and extending forward, and a second cutting part protruding in the one side direction from a front end of the second non-cutting part and configured to be in contact with the first cutting part. When the second lever rotates with respect to the first lever so that the first handle and the second handle move closer to each other in the up-down direction, the first cutting part and the second cutting part are configured to incise the anterior capsule.

In one embodiment, the first cutting part may have a first cutting edge at an upper end of the first cutting part. The second cutting part may have a second cutting edge configured at a lower end of the second cutting part to be in contact with the first cutting edge.

In one embodiment, the first cutting part may include a first flat surface which is a front end surface of the first cutting part. The second cutting part may include a second flat surface which is a rear end surface of the second cutting part.

In one embodiment, in a state where the first cutting part and the second cutting part are in contact with each other, the first flat surface and the second flat surface may be in contact with each other on a same plane.

In one embodiment, the first flat surface and the second flat surface may extend in a direction between a downward direction and a rearward direction.

In one embodiment, in a state where the first cutting part and the second cutting part are in contact with each other, the first cutting part may be positioned at a rear side with reference to the second cutting part, and the first non-cutting part may be positioned in the one side direction with reference to the second non-cutting part.

In one embodiment, the surgical scissors may further include a stopper coupled to the first handle or the second handle and configured to maintain a minimum spacing distance between the first handle and the second handle.

In one embodiment, the first lever may include a first elastic part extending rearward from a rear end of the first handle. The second lever may include a second elastic part extending rearward from a rear end of the second handle. A rear end portion of the first elastic part and a rear end portion of the second elastic part may be connected to each other, so that the first elastic part is configured to be elastically bent convexly upward, and the second elastic part is configured to be elastically bent convexly downward.

In one embodiment, the first lever may include a first rotation shaft support part in which the rotation shaft is positioned between the first handle and the first non-cutting part. The first non-cutting part may extend forward from a lower side portion of the first rotation shaft support part. The second lever may include a second rotation shaft support part in which the rotation shaft is positioned between the second handle and the second non-cutting part. The second non-cutting part may extend forward from an upper side portion of the second rotation shaft support part.

According to the surgical scissors for incising the anterior capsule of the lens according to various embodiments of the present disclosure, an incision direction of the anterior capsule of the lens incised by the first cutting part and the second cutting part is a direction crossing an entry direction of the first lever and the second lever. Therefore, it becomes easy to additionally incise the opening in the anterior capsule of the lens to be closer to a circular shape. As a result, the anterior capsule of the lens can be induced to contract more uniformly into the circular shape, and a phenomenon of the position of an artificial lens moving or the shape of the artificial lens being deformed can be prevented.

DETAILED DESCRIPTION

Figure 1:
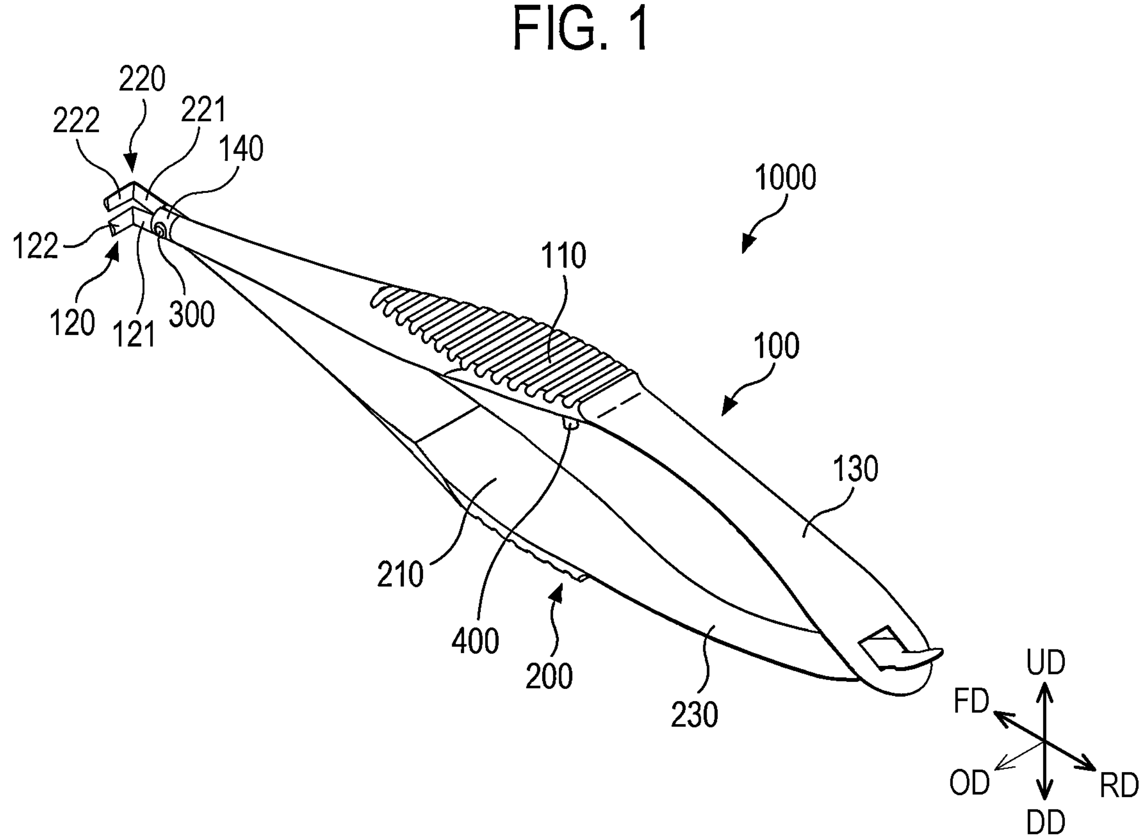
FIG. 1 is a perspective view illustrating surgical scissors for incising an anterior capsule of a lens according to one embodiment of the present disclosure.

Embodiments of the present disclosure are illustrated for the purpose of explaining the technical idea of the present disclosure. The scope of the rights according to the present disclosure is not limited to the embodiments presented below or the detailed descriptions of such embodiments.

All technical terms and scientific terms used in the present disclosure include meanings that are commonly understood by a person of ordinary skill in the art to which the present disclosure belongs unless otherwise defined. All of the terms used in the present disclosure are selected for the purpose of describing the present disclosure more clearly, and are not selected to limit the scope of rights according to the present disclosure.

As used in the present disclosure, expressions such as "including," "comprising," "having," and the like are to be understood as open-ended terms having the possibility of encompassing other embodiments, unless otherwise mentioned in the phrase or sentence containing such expressions.

The singular expressions that are described in the present disclosure may encompass plural expressions unless otherwise stated, which will be also applied to the singular expressions recited in the claims.

The technical idea of the present disclosure has been described heretofore with reference to some embodiments and examples shown in the accompanying drawings. However, it is to be understood that various substitutions, modifications and alterations may be made without departing from the technical idea and scope of the present disclosure that can be understood by those of ordinary skill in the technical field to which the present disclosure pertains. Further, it is to be understood that such substitutions, modifications and alterations fall within the appended claims.

In the present disclosure, where it is mentioned that one element is "connected" or "coupled" to another element, it is to be understood that said one element may be directly connected or coupled to said another element, or may be connected or coupled to said another element via a new additional element.

The directional terms such as "front" and "forward (FD)" used in the present disclosure are based on a direction in which a first and a second blade are positioned with respect to a first handle and a second handle in the accompanying drawings, and the directional terms such as "rear" and "rearward (RD)" refer to the opposite direction. In addition, the directional terms such as "upper," "upper side," and "upward (UD)" are based on a direction in which a first lever is positioned with respect to a second lever in the accompanying drawings, and the directional terms such as "lower," "lower side," and "downward (DD)" refer to the opposite direction. The first and second blades and the first and second handles or the first lever and the second lever illustrated in the accompanying drawings may be oriented differently, and these directional terms may be interpreted accordingly.

Hereinafter, embodiments of the present disclosure will be described with reference to the accompanying drawings. In the accompanying drawings, the same or corresponding components are assigned the same reference numerals. In addition, in the description of the following embodiments, redundant descriptions of the same or corresponding components may be omitted. However, even if descriptions of components are omitted, it is not intended that such components are not included in any embodiment.

Figure 2:
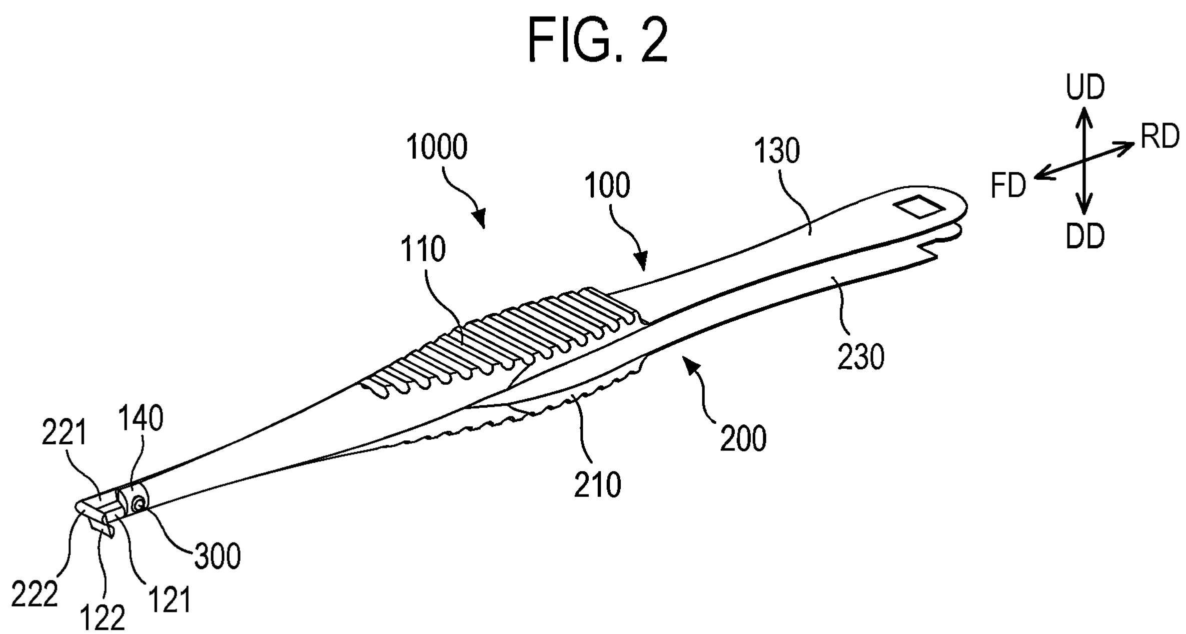
FIG. 2 is a perspective view of the surgical scissors for incising the anterior capsule of the lens shown in FIG. 1, viewed from a different angle, in which rear ends of a first lever and a second lever are separated.
Figure 3:
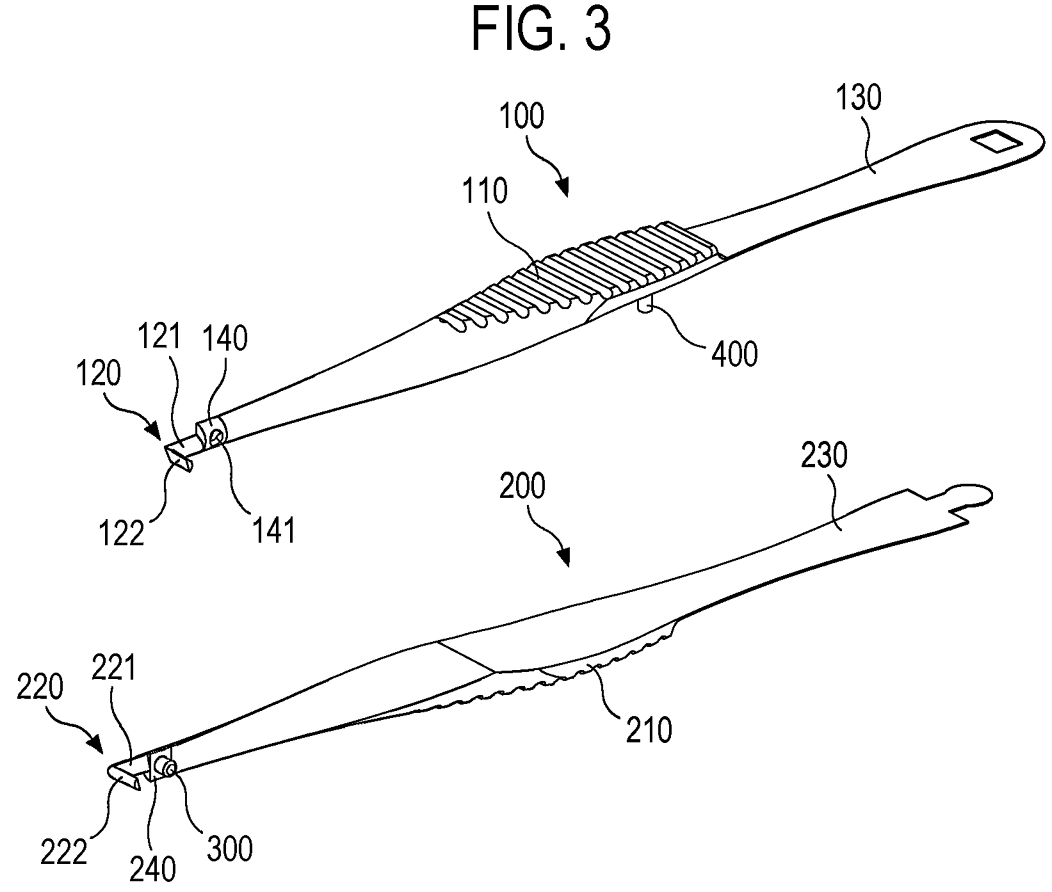
FIG. 3 is an exploded perspective view illustrating the surgical scissors for incising the anterior capsule of the lens shown in FIG. 2.

FIG. 1 is a perspective view illustrating surgical scissors for incising an anterior capsule of a lens according to an embodiment of the present disclosure. FIG. 2 is a perspective view of the surgical scissors for incising the anterior capsule of the lens shown in FIG. 1, viewed from a different angle, in which rear ends of a first lever and a second lever are separated. FIG. 3 is an exploded perspective view illustrating the surgical scissors for incising the anterior capsule of the lens shown in FIG. 2.

As shown in FIGS. 1 to 3, surgical scissors 1000 for incising an anterior capsule of a lens according to an embodiment of the present disclosure (hereinafter, simply referred to as "surgical scissors") include a first lever 100, a second lever 200, and a rotation shaft 300. The surgical scissors 1000 may be made of a metal material. In particular, the surgical scissors 1000 may be made of stainless steel or a titanium alloy for corrosion prevention.

The first lever 100 extends in a front-rear direction (FD-RD) and includes a first handle 110 and a first blade 120. The first handle 110 and the first blade 120 configuring the first lever 100 may be formed integrally. The first lever 100 is configured such that the first handle 110 and the first blade 120 are positioned in opposite directions in an up-down direction (UD-DD) with reference to the rotation shaft 300. For example, the first handle 110 may be positioned at the upper side (UD) with reference to the rotation shaft 300, and the first blade 120 may be positioned at the lower side (DD) with reference to the rotation shaft 300. Therefore, when the first handle 110 moves from the upper side (UD) to the lower side (DD) around the rotation shaft 300, the first blade 120 moves from the lower side (DD) to the upper side (UD) around the rotation shaft 300. Conversely, when the first handle 110 moves from the lower side (DD) to the upper side (UD) around the rotation shaft 300, the first blade 120 moves from the upper side (UD) to the lower side (DD) around the rotation shaft 300.

The first handle 110 is formed at a rear portion with reference to the rotation shaft 300 and extends rearward (RD). The first handle 110 is a portion held by an operator's hand (e.g., a thumb). A plurality of first uneven parts may be formed in at least a portion of an upper surface of the first handle 110 to prevent the operator's hand from slipping. The first uneven parts may extend in a direction parallel to one side direction (OD). The first uneven parts are not limited to the embodiment shown in the drawing and may have various shapes or patterns.

Figures 4, 5:
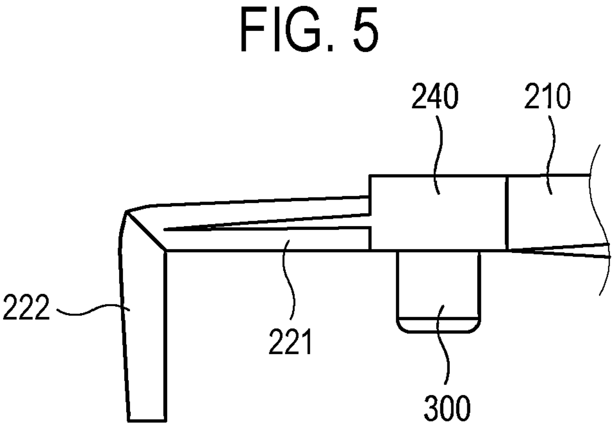
FIG. 4 is a plan view illustrating an enlarged view of a first blade shown in FIG. 3.
FIG. 5 is a plan view illustrating an enlarged view of a second blade shown in FIG. 3.

FIG. 4 is a plan view illustrating an enlarged view of the first blade shown in FIG. 3.

As shown in FIG. 4, the first blade 120 has a first non-cutting part 121 and a first cutting part 122. The first non-cutting part 121 is formed at a front portion with reference to the rotation shaft 300 and extends forward (FD). The first non-cutting part 121 is not directly used for incising the anterior capsule of the lens, and connects the first handle 110 and the first cutting part 122. The first cutting part 122 protrudes in the one side direction (OD) from a front end of the first non-cutting part 121. Here, the one side direction (OD) is a direction crossing the front-rear direction (FD-RD) and the up-down direction (UD-DD). For example, the one side direction (OD) may be configured parallel to the rotation shaft 300 as a direction perpendicular to the front-rear direction (FD-RD) and the up-down direction (UD-DD). The first cutting part 122 may be disposed perpendicular to the first non-cutting part 121. The first non-cutting part 121 and the first cutting part 122 may have an approximate L-shape. The first cutting part 122 is directly used for incising the anterior capsule of the lens. The one side direction (OD) in which the first cutting part 122 protrudes may point in the opposite direction to the direction shown in FIGS. 1 to 3.

The second lever 200 extends in the front-rear direction (FD-RD) and includes a second handle 210 and a second blade 220. The second handle 210 and the second blade 220 configuring the second lever 200 may be formed integrally. The second lever 200 is configured such that the second handle 210 and the second blade 220 are positioned in opposite directions in the up-down direction (UD-DD) with reference to the rotation shaft 300. For example, the second handle 210 may be positioned at the lower side (DD) with reference to the rotation shaft 300, and the second blade 220 may be positioned at the upper side (UD) with reference to the rotation shaft 300. Therefore, when the second handle 210 moves from the lower side (DD) to the upper side (UD) around the rotation shaft 300, the second blade 220 moves from the upper side (UD) to the lower side (DD) around the rotation shaft 300. Conversely, when the second handle 210 moves from the upper side (UD) to the lower side (DD) around the rotation shaft 300, the second blade 220 moves from the lower side (DD) to the upper side (UD) around the rotation shaft 300.

The second handle 210 is formed at a rear portion with reference to the rotation shaft 300 and extends rearward (RD). The second handle 210 is capable of being spaced apart downward from the first handle 110. The second handle 210 is a portion held by the operator's hand (e.g., an index finger and/or middle finger). A plurality of second uneven parts may be formed in at least a portion of a lower surface of the second handle 210 to prevent the operator's hand from slipping. The second uneven parts may extend in a direction parallel to the one side direction (OD). The second uneven parts are not limited to the embodiment shown in the drawing and may have various shapes or patterns.

FIG. 5 is a plan view illustrating an enlarged view of the second blade shown in FIG. 3.

As shown in FIG. 5, the second blade 220 has a second non-cutting part 221 and a second cutting part 222. The second non-cutting part 221 is formed at a front portion with reference to the rotation shaft 300 and extends forward (FD). The second non-cutting part 221 is not directly used for incising the anterior capsule of the lens, and connects the second handle 210 and the second cutting part 222. The second cutting part 222 is configured to protrude in the one side direction (OD) from a front end of the second non-cutting part 221 and to be in contact with the first cutting part 122. The second cutting part 222 may be disposed perpendicular to the second non-cutting part 221. The second cutting part 222 protrudes in the same one side direction (OD) as the first cutting part 122. The second non-cutting part 221 and the second cutting part 222 may have an approximate L-shape. The second cutting part 222 is directly used for incising the anterior capsule of the lens. The one side direction (OD) in which the second cutting part 222 protrudes may point in the opposite direction to the direction shown in FIGS. 1 to 3.

The rotation shaft 300 rotatably connects the first lever 100 and the second lever 200 with respect to each other. As one example, the rotation shaft 300 may be configured such that one end thereof is fixed to one of the first lever 100 and the second lever 200 and an opposite end thereof is rotatable with respect to the other one of the first lever 100 and the second lever 200. As another example, the rotation shaft 300 may be configured to be rotatable with respect to both the first lever 100 and the second lever 200 by forming locking portions, having a diameter larger than that of the rotation shaft 300, at both ends thereof, so as not to be separated from the first lever 100 and the second lever 200. In the following description, the description will focus on a configuration in which one end of the rotation shaft 300 is fixed to the second lever 200, and the opposite end of the rotation shaft 300 is inserted into a through hole 141 (referring to FIG. 3) formed in the first lever 100 so as to be rotatable with respect to the first lever 100.

When the second lever 200 rotates with respect to the first lever 100 around the rotation shaft 300 so that the first handle 110 and the second handle 210 move closer to each other in the up-down direction (UD-DD), the first cutting part 122 and the second cutting part 222 are configured to be in contact with each other to incise the anterior capsule. In this way, an incision direction (that is, the one side direction (OD)) of the anterior capsule of the lens incised by the first cutting part 122 and the second cutting part 222 is perpendicular to an entry direction (that is, forward (FD)) of the first lever 100 and the second lever 200. Therefore, it becomes easy to additionally incise an opening formed in the anterior capsule of the lens to be closer to the circular shape. As a result, since the anterior capsule of the lens is uniformly contracted into the circular shape, the position of an artificial lens is not moved or the shape of the artificial lens is not deformed.

As shown in FIG. 3, in one embodiment, the first cutting part 122 may have a first cutting edge 122*a* at an upper end thereof, and the second cutting part 222 may have a second cutting edge 222*a* configured at a lower end thereof to be in contact with the first cutting edge 122*a*. The first cutting edge 122*a* is formed along an upper edge of the first cutting part 122 and extends parallel to the one side direction (OD). The second cutting edge 222*a* is formed along a lower edge of the second cutting part 222 and extends parallel to the one side direction (OD).

Figure 6:
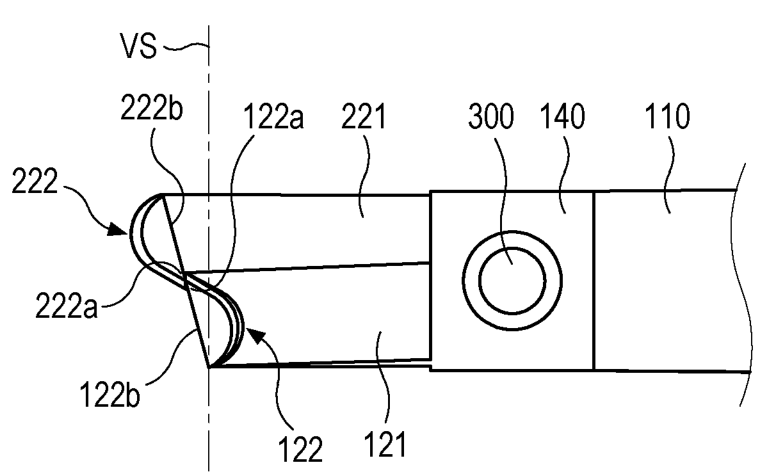
FIG. 6 is a front view illustrating an enlarged view of a first blade and a second blade shown in FIG. 2.

FIG. 6 is a front view illustrating an enlarged view of the first blade and the second blade shown in FIG. 2.

As shown in FIG. 6, in one embodiment, the first cutting part 122 may include a first flat surface 122*b* which is a front end surface of the first cutting part 122, and the second cutting part 222 may include a second flat surface 222*b* which is a rear end surface of the second cutting part 222. A rearwardly convex surface may be formed at a rear end of the first cutting part 122. A cross-section of the first cutting part 122 along the front-rear direction (FD-RD) may have an approximately semicircular shape. A forwardly convex surface may be formed at a front end of the second cutting part 222. A cross-section of the second cutting part 222 along the front-rear direction (FD-RD) may have an approximately semicircular shape. In one embodiment, in a state where the first cutting part 122 and the second cutting part 222 are in contact with each other, the first flat surface 122*b* and the second flat surface 222*b* may be in contact with each other on the same plane.

In one embodiment, the first flat surface 122*b* and the second flat surface 222*b* may extend in a direction between a downward direction (that is, downward (DD)) and a rearward direction (that is, rearward (RD)). As shown in FIG. 6, the first flat surface 122*b* and the second flat surface 222*b* may be inclined to have a predetermined angle with respect to a virtual surface (VS) perpendicular to the front-rear direction (FD-RD).

Figure 7:
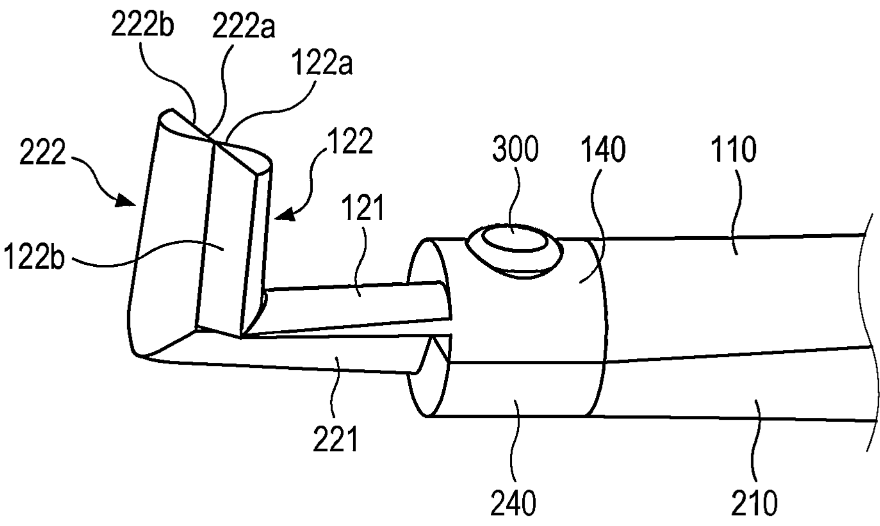
FIG. 7 is a perspective view illustrating the first blade and the second blade shown in FIG. 2 from a different angle.

FIG. 7 is a perspective view illustrating the first blade and the second blade shown in FIG. 2 from a different angle.

As shown in FIG. 7, in one embodiment, in a state where the first cutting part 122 and the second cutting part 222 are in contact with each other, the first cutting part 122 may be positioned rearward (RD) with reference to the second cutting part 222, and the first non-cutting part 121 may be positioned in the one side direction (OD) with reference to the second non-cutting part 221. The first blade 120 including the first non-cutting part 121 and the first cutting part 122 is positioned rearward (RD) and in the one side direction (OD) with reference to the second blade 220 including the second non-cutting part 221 and the second cutting part 222. Due to this configuration, the sizes of the first blade 120 and the second blade 220 of the surgical scissors 1000 can be minimized. Therefore, an incision site in a cornea for entering the surgical scissors 1000 can be minimized. As a result, damage to the cornea can be suppressed or prevented.

The surgical scissors 1000 according to one embodiment may further include a stopper 400 coupled to the first handle 110 or the second handle 210 and configured to maintain a minimum spacing distance between the first handle 110 and the second handle 210. The minimum spacing distance may refer to a maximum distance by which the first handle 110 and the second handle 210 can move closer to each other in order to incise the anterior capsule of the lens. The stopper 400 may be formed by protruding downward (DD) from a lower surface of the first handle 110 or by protruding upward (UD) from an upper surface of the second handle 210.

In one embodiment, the first lever 100 may include a first elastic part 130 extending rearward (RD) from a rear end of the first handle 110, and the second lever 200 may include a second elastic part 230 extending rearward (RD) from a rear end of the second handle 210. In this embodiment, as shown in FIG. 1, a rear end portion of the first elastic part 130 and a rear end portion of the second elastic part 230 may be connected to each other so that the first elastic part 130 is configured to be elastically bent convexly upward (UD), and the second elastic part 230 is configured to be elastically bent convexly downward (DD). When an operator applies a force pressing the first handle 110 and the second handle 210 to move closer to each other, the first elastic part 130 and the second elastic part 230 are elastically deformed. When the operator removes the force pressing the first handle 110 and the second handle 210, the first handle 110 and the second handle 210 return to their original positions by an elastic restoration force of the first elastic part 130 and the second elastic part 230. Since the operator needs to apply a pressure to move the first handle 110 and the second handle 210 only when making an incision, fatigue of the operator due to surgery can be reduced.

Figures 8, 9:
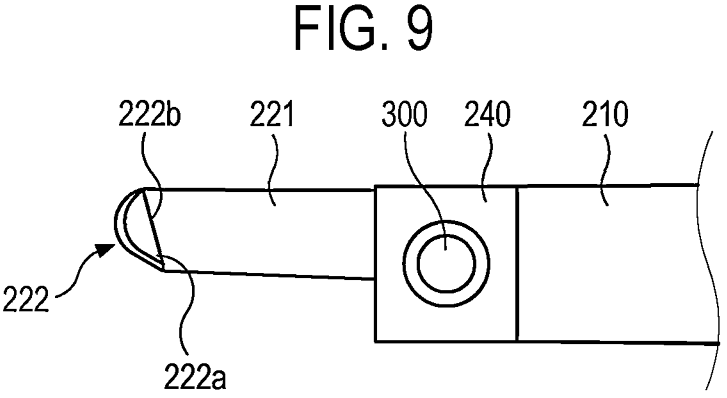
FIG. 8 is a front view illustrating an enlarged view of the first blade shown in FIG. 3.
FIG. 9 is a front view illustrating an enlarged view of the second blade shown in FIG. 3.

FIG. 8 is a front view illustrating an enlarged view of the first blade shown in FIG. 3.

As shown in FIG. 8, in one embodiment, the first lever 100 may further include a first rotation shaft support part 140 in which the rotation shaft 300 is positioned between the first handle 110 and the first non-cutting part 121, and the first non-cutting part 121 may extend forward (FD) from a lower side portion of the first rotation shaft support part 140. The first rotation shaft support part 140 is a portion of a front end of the first handle 110 and may be formed integrally with the first handle 110. The size of the first non-cutting part 121 along the up-down direction (UD-DD) is smaller than that of the first rotation shaft support part 140.

FIG. 9 is a front view illustrating an enlarged view of the second blade shown in FIG. 3.

As shown in FIG. 9, in this embodiment, the second lever further includes a second rotation shaft support part 240 in which the rotation shaft 300 is positioned between the second handle 210 and the second non-cutting part 221, and the second non-cutting part 221 may extend forward (FD) from an upper side portion of the second rotation shaft support part 240. The second rotation shaft support part 240 is a portion of a front end of the second handle 210 and may be formed integrally with the second handle 210. The size of the second non-cutting part 221 along the up-down direction (UD-DD) is smaller than that of the second rotation shaft support part 240.

Since the first non-cutting part 121 is positioned in a lower side portion of the first rotation shaft support part 140 and the second non-cutting part 221 is positioned in the upper side portion of the second rotation shaft support part 240, in a state where the first cutting part 122 and the second cutting part 222 are in contact with each other, the sizes of the first non-cutting part 121 and the second non-cutting part 221 along the up-down direction may be the same as the size of the first rotation shaft support part 140 or the size of the second rotation shaft support part 240. Due to this configuration, the sizes of the first blade 120 and the second blade 220 of the surgical scissors 1000 can be minimized. Therefore, the incision site in the cornea for entering the surgical scissors 1000 can be minimized. As a result, damage to the cornea can be suppressed or prevented.

The technical idea of the present disclosure has been described heretofore with reference to some embodiments and examples shown in the accompanying drawings. However, it is to be understood that various substitutions, modifications and alterations may be made without departing from the technical idea and scope of the present disclosure that can be understood by those of ordinary skill in the technical field to which the present disclosure pertains. Further, it is to be understood that such substitutions, modifications and alterations fall within the scope of the appended claims.

What is claimed is:

1. Surgical scissors for incising an anterior capsule of a lens, the surgical scissors comprising:

a first lever extending in a front-rear direction;

a second lever extending in the front-rear direction; and a rotation shaft configured to rotatably connect the first lever and the second lever to each other, wherein the first lever includes:

a first handle formed at a rear portion with reference to the rotation shaft; and a first blade having a first non-cutting part formed at a front portion with reference to the rotation shaft and extending forward, and a first cutting part protruding in one side direction crossing the front-rear direction and an up-down direction from a front end of the first non-cutting part, wherein the second lever includes:

a second handle formed at the rear portion with reference to the rotation shaft and capable of being spaced downward from the first handle; and a second blade having a second non-cutting part formed at a front portion with reference to the rotation shaft and extending forward, and a second cutting part protruding in the one side direction from a front end of the second non-cutting part and configured to be in contact with the first cutting part, and wherein when the second lever rotates with respect to the first lever so that the first handle and the second handle move closer to each other in the up-down direction, the first cutting part and the second cutting part are configured to incise the anterior capsule.

2. The surgical scissors of claim 1, wherein the first cutting part has a first cutting edge at an upper end of the first cutting part, and wherein the second cutting part has a second cutting edge configured at a lower end of the second cutting part to be in contact with the first cutting edge.

3. The surgical scissors of claim 1, wherein the first cutting part includes a first flat surface which is a front end surface of the first cutting part, and wherein the second cutting part includes a second flat surface which is a rear end surface of the second cutting part.

4. The surgical scissors of claim 3, wherein in a state where the first cutting part and the second cutting part are in contact with each other, the first flat surface and the second flat surface are in contact with each other on a same plane.

5. The surgical scissors of claim 4, wherein the first flat surface and the second flat surface extend in a direction between a downward direction and a rearward direction.

6. The surgical scissors of claim 1, wherein in a state where the first cutting part and the second cutting part are in contact with each other, the first cutting part is positioned at a rear side with reference to the second cutting part, and the first non-cutting part is positioned in the one side direction with reference to the second non-cutting part.

7. The surgical scissors of claim 1, further comprising a stopper coupled to the first handle or the second handle and configured to maintain a minimum spacing distance between the first handle and the second handle.

8. The surgical scissors of claim 1, wherein the first lever comprises a first elastic part extending rearward from a rear end of the first handle, wherein the second lever comprises a second elastic part extending rearward from a rear end of the second handle, and wherein a rear end portion of the first elastic part and a rear end portion of the second elastic part are connected to each other, so that the first elastic part is configured to be elastically bent convexly upward, and the second elastic part is configured to be elastically bent convexly downward.

9. The surgical scissors of claim 1, wherein the first lever includes a first rotation shaft support part in which the rotation shaft is positioned between the first handle and the first non-cutting part, wherein the first non-cutting part extends forward from a lower side portion of the first rotation shaft support part, wherein the second lever includes a second rotation shaft support part in which the rotation shaft is positioned between the second handle and the second non-cutting part, and wherein the second non-cutting part extends forward from an upper side portion of the second rotation shaft support part.

* * * * *